(12) United States Patent
Chen et al.

(10) Patent No.: US 11,123,421 B2
(45) Date of Patent: Sep. 21, 2021

(54) COLD ADAPTED AND VIRULENCE FACTOR DELETED LIVE ATTENUATED VACCINE SUITABLE FOR MUCOSAL DELIVERY

(71) Applicant: VERSITECH LIMITED, Hong Kong (HK)

(72) Inventors: Honglin Chen, Hong Kong (HK); Min Zheng, Hong Kong (HK); Pui Wang, Hong Kong (HK); Johnson Yiu-Nam Lau, Houston, TX (US); Kwok Yung Yuen, Hong Kong (HK)

(73) Assignee: VERSITECH LIMITED

( * ) Notice: Subject to any disclaimer, the term of this patent is extended or adjusted under 35 U.S.C. 154(b) by 0 days.

(21) Appl. No.: 16/094,780

(22) PCT Filed: Apr. 18, 2017

(86) PCT No.: PCT/US2017/028170
§ 371 (c)(1),
(2) Date: Oct. 18, 2018

(87) PCT Pub. No.: WO2017/184626
PCT Pub. Date: Oct. 26, 2017

(65) Prior Publication Data
US 2019/0125858 A1 May 2, 2019

Related U.S. Application Data

(60) Provisional application No. 62/324,134, filed on Apr. 18, 2016.

(51) Int. Cl.
*A61K 39/145* (2006.01)
*A61K 39/12* (2006.01)
*A61K 39/00* (2006.01)

(52) U.S. Cl.
CPC ............ *A61K 39/145* (2013.01); *A61K 39/12* (2013.01); *A61K 2039/5254* (2013.01); *A61K 2039/5256* (2013.01); *C12N 2760/16134* (2013.01); *C12N 2760/16162* (2013.01); *C12N 2770/20034* (2013.01); *Y02A 50/30* (2018.01)

(58) Field of Classification Search
None
See application file for complete search history.

(56) References Cited

U.S. PATENT DOCUMENTS 7,758,867 B2    7/2010  Seong et al.
2004/0253273 A1 12/2004 Paleso et al.

OTHER PUBLICATIONS

Donis. R. O. et al., Performance characteristic of qualified cell lines for isolation and propagation of influenza viruses for vaccine manufacturing, Vaccine, 2014, vol. 32, pp. 6583-6590.
A Garcia-Sastre, A. et al., Influenza A virus lacking the NS1 gene replicates in interferon-deficient systems, Virology, 1998, vol. 252. pp. 324-330.
PCT Search Report and Written Opinion dated Jul. 11, 2017 for PCT/US2017/028170 filed on Apr. 18, 2017 entitled Cold Adapted and Virulence Factor Deleted Live Attenuated Vaccine Suitable for Mucosal Delivery (Applicants: Emerging Viral Vaccine (HK) Limited and Versitech Limited).
Zheng, M.. Study on function of NS1 protein in influenza A virus replication and vaccine application of DeINS1 viruses, Thesis for the degree of Doctor of Philosophy at the University of Hong Kong, 2015, pp. i-x, 1-170.

*Primary Examiner* — Benjamin P Blumel
(74) *Attorney, Agent, or Firm* — Pabst Patent Group LLP

(57) ABSTRACT

Compositions and methods are provided for a live, attenuated influenza vaccine suitable for nasal administration. The vaccine utilizes a cold adapted influenza virus that lacks virulence factor, and includes mutations that provide replicative ability sufficient for vaccine manufacture. Vaccines so produced provide significant cross protection for non-vaccinating strains. The vaccine is safe for children under the age of 2 and adults over 49 years of age. In addition, the cold adapted, virulence factor deleted influenza virus can be adapted to provide immunity to non-influenza pathogens.

9 Claims, 12 Drawing Sheets
Specification includes a Sequence Listing.

SEQUENCE LISTING

```
<160> NUMBER OF SEQ ID NOS: 4

<210> SEQ ID NO 1
<211> LENGTH: 19
<212> TYPE: DNA
<213> ORGANISM: Artificial Sequence
<220> FEATURE:
<223> OTHER INFORMATION: NP mutation of H1N1 influenza virus at G346A
      (D101N)

<400> SEQUENCE: 1
agagtagacg gaaagtgga                                              19

<210> SEQ ID NO 2
<211> LENGTH: 61
<212> TYPE: DNA
<213> ORGANISM: Artificial Sequence
<220> FEATURE:
<223> OTHER INFORMATION: NEP mutations of H1N1 influenza virus at T261G
      (L79V) and A310G (E95G)

<400> SEQUENCE: 2
aggtggttaa ttgaagaaat gcggcacaga ttgaaagcga cagagaatag tttcgaacaa    60
a                                                                    61

<210> SEQ ID NO 3
<211> LENGTH: 20
<212> TYPE: DNA
<213> ORGANISM: Artificial Sequence
<220> FEATURE:
<223> OTHER INFORMATION: Forward primer for DelNS1 H1N1 strain (CA04-
      DelNSA-529F)

<400> SEQUENCE: 3
gacatactta tgaggatgtc                                              20

<210> SEQ ID NO 4
<211> LENGTH: 22
<212> TYPE: DNA
<213> ORGANISM: Artificial Sequence
```

```
<220> FEATURE:
<223> OTHER INFORMATION: Reverse primer for H1N1 DelNS1 strain (CA04-
      DelNS1-56R)

<400> SEQUENCE: 4
ctgaaagctt gacatggtgt tg                                              22
```

COLD ADAPTED AND VIRULENCE FACTOR DELETED LIVE ATTENUATED VACCINE SUITABLE FOR MUCOSAL DELIVERY

This application claims priority to U.S. Provisional Application No. 62/324,134 filed on Apr. 18, 2016. These and all other referenced extrinsic materials are incorporated herein by reference in their entirety. Where a definition or use of a term in a reference that is incorporated by reference is inconsistent or contrary to the definition of that term provided herein, the definition of that term provided herein is deemed to be controlling.

FIELD OF THE INVENTION

The field of the invention is vaccines, specifically vaccines providing protection from viral illness.

BACKGROUND

The following description includes information that may be useful in understanding the present invention. It is not an admission that any of the information provided herein is prior art or relevant to the presently claimed invention, or that any publication specifically or implicitly referenced is prior art.

Annual epidemics and pandemics of influenza (flu) pose a significant disease and health burden, with significant mortality due to complications. It is estimated that, annually, 5-10% of adults and 20-30% of children become infected with seasonal flu viruses. Among those so infected 2 to 5 million may have severe disease, while as many as 500,000 are fatal each year. This represents a significant health burden globally.

Vaccination with flu vaccine is considered to be the most effective way to alleviate disease burden and mortality caused by seasonal influenza, as well as to prevent further/future pandemics in humans. Currently there are two types of flu vaccines in the market, split (i.e. non-viable virus) vaccines (which are available from several manufacturers) and cold-adapted attenuated (i.e. live virus) vaccines (for example, Flumist® from Medimmune®). Disadvantages have long been recognized for both vaccine approaches.

Current split flu vaccines cannot be ready in a short timeframe, and therefore are of limited utility in responding to rapidly emerging strains. For example, in the 2009 pandemic it took nearly 9-12 months to deliver first batch of human vaccine. Moreover, poor immunogenicity is well known for split vaccines. This is particularly true among older adults and young children. In addition, split vaccines are generally restricted to specific subtypes. They are typically unsatisfactory to totally ineffective in providing protection across intra-genotypic and cross-genotypic subtypes. As a result a more immunogenic vaccine approach that can generate a higher titer of neutralizing antibodies against common viral epitopes that can offer protection against both viruses within the same genotype or subtypes are urgently needed.

In contrast, current cold adapted live attenuated vaccines (LAIV) have improved immunogenicity relative to split vaccines. Such live attenuated vaccines, however, are currently only approved for use in people between 2 to 49 years old (due to the potential breakthrough in those less than 2 years old or older than 49). Unfortunately, it is the very young and older adults for whom such a vaccine has the most value. It should also be appreciated that, based on CDC preliminary data, from 2013 through 2016 LAIV formulation showed relatively poor or relatively lower effectiveness. This has limited the benefits of flu vaccines for the most needed populations. The quick production of low cost, abundant, and effective vaccines (capable of inducing a robust immune response) is important for intervention and prevention of influenza, particularly seasonal influenza in young children and the elderly.

Since the first documentation of human infections with avian H5N1 virus in Hong Kong in 1997, human infections with other subtypes of avian influenza virus, including H9N2, H7N7, H6N1, H7N9, H5N6, and H10N8, have been reported in countries in which these subtypes of avian influenza virus are circulating among poultry. Among these emerging influenza viruses, 858 human infections with H5N1 virus have been identified from 16 countries since 2003; among these 453 were fatal (http://www.who.int/influenza/human_animal_interface/2017_03_1_table H5N1.pdf?ua=1). All publications herein are incorporated by reference to the same extent as if each individual publication or patent application were specifically and individually indicated to be incorporated by reference. Where a definition or use of a term in an incorporated reference is inconsistent or contrary to the definition of that term provided herein, the definition of that term provided herein applies and the definition of that term in the reference does not apply.

While the H5N1 virus and its derivatives (H5N6 and H5N2) are continuing to spread and cause human infections, the emergence of H7N9 virus in China in 2013 has also caused more than a thousand human cases, about 30% of which have been fatal (http://www.wpro.who.int/outbreaks_emergencies/H7N9/en/). Sporadic cases of H7N9 infection are continuing to emerge in China and there are concerns that this subtype may pose a greater threat of a potential pandemic than the H5N1 virus. Human infections with other emerging subtypes of avian influenza virus, such as H10N8 and H6N1, have also been reported in China. There is a concern that some of these subtypes may gain further adaptation in humans or become reassortant with seasonal flu virus and cause a new pandemic.

The experience of the 2009 pandemic of H1N1 showed preparation of vaccine for human vaccination from the emergence of a virus sometimes takes more than 6 months before availability to the public. Current flu vaccine development will not meet the requirement for the nature of rapid dissemination of pandemic influenza. It is a certainty that there will be new pandemics in the future; even though it is impossible to predict the timing and subtype of virus.

Live attenuated influenza (flu) vaccines with enhanced immunogenicity have the potential to meet the requirements for seasonal and pandemic vaccines. Live attenuated flu vaccines have several advantages over the split or inactivated vaccines. First of all, live attenuated vaccines are able to induce better immune responses in recipients. Secondly, live attenuated vaccines can use less vaccine for immunization. Finally, attenuated live flu vaccines can be easily applied through nasal administration. Current attenuated flu vaccines, however, may not provide complete protection, and are not approved for use in very young and older populations where they are most needed.

Use of influenza viruses cold adapted through passage at reduced temperatures in vaccines has also been attempted. For example, U.S. Pat. No. 7,758,867, to Seong, describes the use of a viral strain carrying six copies of an H1N1 influenza virus genome that has been cold adapted in vaccines. All publications identified herein are incorporated by reference to the same extent as if each individual publication or patent application were specifically and individually indicated to be incorporated by reference. Where a definition or use of a term in an incorporated reference is inconsistent or contrary to the definition of that term provided herein, the definition of that term provided herein applies and the definition of that term in the reference does not apply. Similarly, U.S. Pat. No. 8,282,937, to Maassab and Herlocher, describes the use of cold adapted H1N1 influenza viruses carrying certain specified mutations as a tool for producing vaccines to endemic influenza viruses. It is not clear, however, if such cold adapted viruses provide long term protection for influenza strains beyond that of the parent serotype.

U.S. Pat. No. 8,591,914, to Yang and Kemble, discusses multivalent vaccines produced using reassortant influenza viruses as a potential approach to immunization against multiple influenza serotypes, and mentions that such reassortant strains can be cold adapted. It is unclear, however, if such an approach can provide adequate safety for the very young and older populations.

Thus, there is still a need for a safe and effective attenuated vaccine suitable for use in preventing human infection, particularly with an influenza virus.

SUMMARY OF THE INVENTION

The inventive subject matter provides apparatus, systems and methods for generation of an attenuated and cold adapted influenza virus that lacks a virulence factor yet reproduces effectively for vaccine manufacture. Such a virus can be used to manufacture a vaccine suitable for vaccination via the nasal route. The vaccine is safe for use in individual less than 2 years old and older than 49 years of age, and provides significant cross protection. The attenuated and cold adapted virus can also be adapted through genetic modification to provide immunity to non-influenza pathogens.

One embodiment of the inventive concept is a mutated influenza virus for vaccine production. The virus includes a H1N1 influenza virus genome that includes a deletion of a virulence factor activity, a first set of one or more mutation(s) that confers replication at 37° C. in the absence of the virulence factor activity, and a second set of one or more mutation(s) that confers replication at a temperature below 35° C. The deletion of virulence factor activity can include a deletion of at least part of a virulence factor gene. Such a deletion can be a deletion of at least part of an NS1 gene extending beyond nucleotides 57 to 528 of an NS1 segment of the mutated virus. The first set of one or more point mutation(s) that confer replicative competence, which can lie outside of an M region of the mutated H1N1 influenza virus (for example, a G346A mutation in the H1N1 influenza virus genome). The second set of one or more mutation(s) can include one or more point mutation(s), such as a T261G or a A310G mutation in the H1N1 influenza virus genome.

Such a mutated influenza virus can also include a third set of one or more mutation(s) that confers replication at a temperature below 35° C. These can include one or more point mutation(s) that are distinct from the second set of mutation(s), such as a T261G or an A310G mutation in the H1N1 influenza virus genome. The mutated influenza virus can show reduced replicative ability, relative to a temperature of 35° C. or lower, at a temperature of 37° or higher.

In some embodiments the mutated influenza virus includes an insertion of a gene encoding for an exogenous antigen. Such an exogenous antigen can be derived from a human pathogen, for example a virus (e.g. an influenza virus, a SARS virus, a MERS virus, a Zika virus, a hepatitis virus, a papilloma virus, and an Ebola virus), a bacteria, a fungus, and/or a parasite. In other embodiments the mutated influenza virus includes an insertion of a gene encoding for an endogenous antigen that is associated with a disease state, such as a cancer-associated antigen and a tau protein associated with Alzheimer's disease.

Another embodiment of the inventive concept is a mutated influenza virus as described above, where the mutated influenza virus is suitable for use in the formulation of a live, attenuated vaccine. Such a live, attenuated vaccine is suitable for vaccination via exposure of a mucous membrane to the live, attenuated vaccine.

Another embodiment of the inventive concept is a live, attenuated vaccine that includes a modified H1N1 influenza virus having a genome having a deletion of a virulence factor activity, a first set of one or more mutation(s) that confers replication in the absence of the virulence factor activity, and a second set of one or more mutation(s) that confers replication at a temperature below 35° C. The modified H1N1 influenza virus is present in the vaccine in sufficient quantities to provide a protective effect upon immunization. The vaccine includes a vehicle, and is formulated to support vaccination by contact of a mucous membrane with the live, attenuated vaccine. In some embodiments the deletion of virulence factor activity includes a deletion of at least part of a virulence factor gene, such as a deletion of at least part of an NS1 gene extending beyond nucleotides 57 to 528 of an NS1 segment of the mutated virus. In some embodiments the first set of one or more mutation(s) includes a first set of one or more point mutation(s)) that provide replicative competence; these can lie outside of an M region of the modified H1N1 influenza virus (for example, a G346A mutation in the H1N1 influenza virus genome). In some embodiments the second set of one or more mutation(s) comprises a second set of one or more point mutation(s), such as a T261G and/or an A310G mutation in the H1N1 influenza virus genome. The modified virus utilized in a live, attenuated vaccine of the inventive concept can include a third set of one or more mutation(s) that provide for replication at a temperature below 35° C., such as a T261G and/or an A310G mutation in the H1N1 influenza virus genome. Such a mutated influenza virus shows reduced replicative ability, relative to a temperature of 35° C. or lower, at a temperature of 37° or higher.

In some embodiments the attenuated vaccine includes a mutated influenza virus having an insertion of a gene encoding for an exogenous antigen, such as a human pathogen. Examples of suitable human pathogens include a virus (e.g. an influenza virus, a SARS virus, a MERS virus, a Zika virus, a hepatitis virus, a papilloma virus, and an Ebola virus), a bacteria, a fungus, and a parasite. In other embodiments the attenuated vaccine includes a mutated influenza virus having of a gene encoding for an endogenous antigen that is associated with a disease state, such as a cancer-associated antigen and/or a tau protein.

As noted above, a vaccine of the inventive concept can include a vehicle. In some embodiments this vehicle includes an adjuvant and/or an immune enhancer. Examples of suitable immune enhancers include TLR-7 agonists, such as imiquimod.

Due at least in part to the lack of a virulence factor and adaptation to reduced temperatures, the live, attenuated vaccine is safe for use in a human under two years of age and/or greater than 49 years of age. The live, attenuated vaccine is effective in providing an at least 20% survival rate in an animal model that has been inoculated with a high lethal dose of a pathogen for which the live, attenuated vaccine provides protection, where such inoculation occurs at least two weeks after an intranasal vaccination of the animal model with the live, attenuated vaccine.

Another embodiment of the inventive concept is a method of generating a modified influenza virus suitable for use in a live, attenuated vaccine. Such a method includes deleting a virulence factor activity from an H1N1 influenza virus to generate a first mutated virus; propagating the first mutated virus in a mammalian cell line at 37° or greater to generate a replication competent second mutated virus that includes a first set of one or more mutation(s), and propagating the second mutated virus in an avian egg system at a temperature of less than 35° C. to generate a cold adapted third mutated virus comprising a second set of one or more mutation(s). In some embodiments the deletion of virulence factor activity includes a deletion of at least part of an NS1 gene, and wherein the deletion extends beyond nucleotides 57 to 528 of an NS1 segment. In some embodiments the first set of one or more mutation(s) is a first set of one or more point mutation(s) that confer replicative competence, which can lie outside of an M region of the mutated H1N1 influenza virus (e.g. a G346A mutation in the H1N1 influenza virus genome). The second set of one or more mutation(s) is a second set of one or more point mutation(s), such as a T261G and/or an A310G mutation in the H1N1 influenza virus genome. In some embodiments the third mutated virus comprises a third set of one or more mutation(s) that is distinct from the second set of mutations and that confers replication at a temperature below 35° C., such as a T261G and/or an A310G mutation in the H1N1 influenza virus genome. The third mutant virus can show reduced replicative ability, relative to a temperature of 35° C. or lower, at a temperature of 37° or higher.

Some embodiments include the step of inserting a gene encoding for an exogenous antigen into H1N1 influenza virus. In such embodiments the exogenous antigen can be derived from a human pathogen, such as a virus (e.g. an influenza virus, a SARS virus, a MERS virus, a Zika virus, a hepatitis virus, a papilloma virus, and an Ebola virus), a bacteria, a fungus, and/or a parasite. In other embodiments a gene encoding for an endogenous antigen that is associated with a disease state is inserted, such as a cancer-associated antigen and/or a tau protein.

Various objects, features, aspects and advantages of the inventive subject matter will become more apparent from the following detailed description of preferred embodiments, along with the accompanying drawing FIGS. in which like numerals represent like components.

BRIEF DESCRIPTION OF THE DRAWINGS

FIG. 1 schematically depicts an exemplary process for generation of a replication competent and cold adapted DelNS1 influenza virus (Cold adapted CA04-DelNS1).

FIG. 12 Shows photographs of lung histology of Adv-PP4 treated mice receiving cold adapted DelNS1 influenza virus carrying a MERS antigen gene as a vaccine or a PBS sham vaccine, following infection with a MERS Coronavirus.

DETAILED DESCRIPTION

Figure 2:
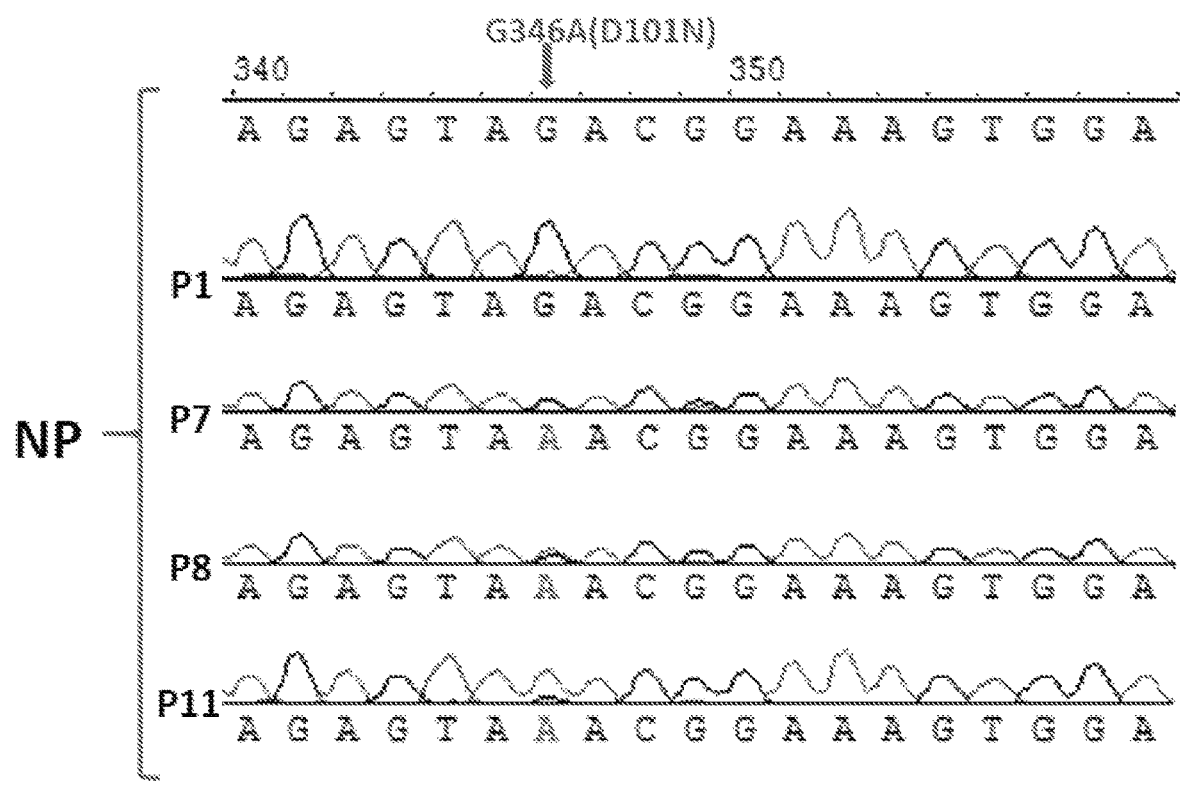
FIG. 2 depicts sequencing data showing a mutation in NP at G346A (D101N) position, which has been found to support DelNS1 virus replication in MDCK cells and embryonated chicken eggs despite the deletion of a virulence factor.

The following description includes information that may be useful in understanding the present invention. It is not an admission that any of the information provided herein is prior art or relevant to the presently claimed invention, or that any publication specifically or implicitly referenced is prior art. The following discussion provides many example embodiments of the inventive subject matter. Although each embodiment represents a single combination of inventive elements, the inventive subject matter is considered to include all possible combinations of the disclosed elements. Thus if one embodiment comprises elements A, B, and C, and a second embodiment comprises elements B and D, then the inventive subject matter is also considered to include other remaining combinations of A, B, C, or D, even if not explicitly disclosed.

The inventive subject matter describes the development of mutations that are essential for a DelNS1 virus to have efficient replication, and also the mutation for providing cold-adaptation for the DelNS1 virus. NS1 is a virulence gene of influenza viruses, with the NS1 protein playing an important role in antagonizing host antiviral response and supporting virus replication. Efficient replication provided by these specific mutations is essential for high virus production, which is an essential element for the development of influenza vaccine. Cold adaptation of the immunizing virus provided by these specific mutations facilitates use as an attenuated live vaccine, for example a vaccine that can be conveniently and safely administered through the respiratory tract (e.g. nasally or by inhalation).

This invention also describes the development of the newly discovered and developed virus into a vaccine. This invention also describes the improved safety and also surprisingly great efficacy of this newly developed vaccine. The inventors contemplate that a vaccine based on a DelNS1 virus having these specific mutations can also be safely used in persons under two years of age and over 50 years of age.

One should appreciate that the disclosed techniques provide many advantageous technical effects including improved protection to various strains of influenza virus and an improved safety profile for very young and elderly populations.

It should also be appreciated that the convenience of intra-nasal or mucosal application (in providing protection without the discomfort associated with injections) coupled with the disclosed improved safety and better efficacy/protection to various strains of influenza virus, particularly when further coupled with the use of an immune enhancer. Suitable immune enhancers include TLR-7 agonists. In a preferred embodiment, the immune enhancer is imiquimod (which has been demonstrated to further enhance the immune response to influenza vaccine). Use of such intra-nasal or mucosal application further enhances the overall utility and protection of the general population—including the very young (i.e. less than 2 years of age) and elderly (i.e. older than 49 years of age) populations.

In some embodiments, the numbers expressing quantities of ingredients, properties such as concentration, reaction conditions, and so forth, used to describe and claim certain embodiments of the invention are to be understood as being modified in some instances by the term "about." Accordingly, in some embodiments, the numerical parameters set forth in the written description and attached claims are approximations that can vary depending upon the desired properties sought to be obtained by a particular embodiment. In some embodiments, the numerical parameters should be construed in light of the number of reported significant digits and by applying ordinary rounding techniques. Notwithstanding that the numerical ranges and parameters setting forth the broad scope of some embodiments of the invention are approximations, the numerical values set forth in the specific examples are reported as precisely as practicable. The numerical values presented in some embodiments of the invention may contain certain errors necessarily resulting from the standard deviation found in their respective testing measurements.

As used in the description herein and throughout the claims that follow, the meaning of "a," "an," and "the" includes plural reference unless the context clearly dictates otherwise. Also, as used in the description herein, the meaning of "in" includes "in" and "on" unless the context clearly dictates otherwise.

The recitation of ranges of values herein is merely intended to serve as a shorthand method of referring individually to each separate value falling within the range. Unless otherwise indicated herein, each individual value is incorporated into the specification as if it were individually recited herein. All methods described herein can be performed in any suitable order unless otherwise indicated herein or otherwise clearly contradicted by context. The use of any and all examples, or exemplary language (e.g. "such as") provided with respect to certain embodiments herein is intended merely to better illuminate the invention and does not pose a limitation on the scope of the invention otherwise claimed. No language in the specification should be construed as indicating any non-claimed element essential to the practice of the invention.

Groupings of alternative elements or embodiments of the invention disclosed herein are not to be construed as limitations. Each group member can be referred to and claimed individually or in any combination with other members of the group or other elements found herein. One or more members of a group can be included in, or deleted from, a group for reasons of convenience and/or patentability. When any such inclusion or deletion occurs, the specification is herein deemed to contain the group as modified thus fulfilling the written description of all Markush groups used in the appended claims.

In some embodiments of the inventive concept expression of a virulence factor can be decreased and/or eliminated in an immunizing virus strain. In a preferred embodiment this is accomplished by deleting all or part of a virulence factor gene (for example, a gene encoding an NS1 protein). An example of an influenza virus strain from which a virulence factor has been deleted is DelNS1, from which an intron encoding for the NS1 protein has been excised. Such a deletion necessarily has a deleterious effect on the ability of the resulting virus to replicate and propagate. Surprisingly Inventors have found that passage through a mammalian cell line at 37° C. results in the propagation of such virulence factor-deleted influenza viruses with additional mutations that confer efficient replication in the absence of the virulence factor. Such mutations can be unique to supporting replication in the absence of the virulence factor gene.

While a lack of virulence with an ability to replicate is a useful feature for an influenza virus intended for use as a vaccine, additional features that can reduce the probability systemic infection following inoculation can be useful. Inventors have found that subsequent passage of a virus carrying such a virulence factor deletion mutation at reduced temperatures (for example, through embryonic chicken eggs at 30° permits isolation of a cold adapted DelNS1 virus. Replication of such cold adapted virus strains is inhibited at normal body temperatures (e.g. 37° C.), effectively isolating replicating populations to areas of the body with relatively low temperatures (such as the nasal cavity).

Such cold adapted DelNS1 viruses were found to be avirulent, and able to provide more effective protection to lethal challenge from heterosubtypic viruses than prior art (i.e. commercially available) cold adapted live attenuated influenza vaccine. Since the virulence element is deleted from such a cold adapted DelNS1 virus genome and the virus is additionally adapted to replicate at a lower temperature than those found in prior art attenuated virus influenza vaccine strain, a vaccine prepared using viruses of the inventive concept is safer and able to be used among the most vulnerable populations—the elderly and young children.

Specifically, the inventors have found that passage through a mammalian cell line (for example MDCK cells) at conventional temperatures (e.g. 37° C.) of an influenza virus engineered by deletion of a virulence gene (for example, NS1) can provide mutations that support efficient replication of the virus, despite lack of the virulence factor. Inventors have further found that passage of such a mutated virus through host cells (such as are found in embryonic eggs) at reduced temperatures (i.e. less than 37° C.) can provide additional mutations that confer cold adaptation. Such reduced temperatures can be about 35° C., about 33° C., about 30° C., about 27° C., or less than 27° C.

The inventive subject matter provides apparatus, systems and methods in which a vaccine strain which can overcome the limitations of the current influenza vaccines and which will meet the requirements of needed population for seasonal flu and for pandemic preparedness. Such vaccines can be developed using a live attenuated virus carrying mutations that: (1) delete a virulence factor, (2) provide efficient replication in the absence of the virulence factor, and (3) provide cold adaptation. The inventive concept includes three components. First, a DelNS1 attenuated influenza virus (e.g. influenza virus with non-structural gene 1 deleted) was developed that surprisingly included a novel mutation in the M segment of the genome that allows the efficient reproduction of the virus in the absence of the virulence factor. Such efficient reproduction is essential for practical manufacture of an influenza vaccine. Second, it was surprisingly found that such a mutant virus can be further cold-adapted. This finding permitted development a series of new mutations that provided cold-adaptation of the virulence factor deleted influenza virus. Such cold adaptation can confer the ability to deliver a vaccine preparation of the virus effectively by a respiratory or mucous membrane route. Even more surprising, it was that the virus strain developed through such a two pronged modification process (i.e. NS1 deletion and cold-adaptation with the newly discovered mutations) can still produce a high viral titer; a feature that is very useful for vaccine production. Finally, with such a double modifications and a cold adaptation that permits a vaccine prepared using such a highly modified virus to be a useful when delivered intra-nasally, the inventors found that a vaccine produced this fashion showed an excellent safety profile in animal studies, surprisingly improved cross reactivity against other (i.e. non-immunizing) influenza strains, and are more effective than prior intra-nasal vaccine gold-standard (including the only intranasal influenza vaccine available for human subjects).

Inventors have also found that the immunogenicity of such an influenza vaccine can be augmented for both the same strain and cross-species with the concomitant use of imiquimod. Use of imiquimod and similar compounds to enhance immunogenicity of various vaccinating compositions is described in U.S. Provisional Patent Application No. 62/194,136, filed Jul. 17, 2015.

In one embodiment of the inventive concept, an influenza virus that has been modified by deletion of a virulence factor, followed by development of at least one mutation that permits efficient replication in the absence of the virulence factor and at least one additional mutation that provides cold adaptation serves as a vehicle or "backbone" for insertion of one or more genes derived from a non-influenza pathogen. Such a modified virus can serve as the basis of a live, attenuated vaccine that provides clinically effective protection against and/or treatment of infection by the non-influenza pathogen. In a preferred embodiment such a vaccine can be effectively administered via a mucous membrane. Examples of suitable non-influenza pathogens include SARS, MERS, Zika virus, hepatitis virus, papilloma virus, Ebola virus and others. In particular Inventors have found that insertion of a MERS RBD domain into such a modified influenza virus backbone can be used in a nasally administered vaccine that confers protection from MERS infection to DPP4-transduced mice. Such DPP4-transduced mice are commonly utilized as murine models for MERS vaccine development. Inventors have also successfully incorporated a Zika virus RBD domain into such a modified influenza virus backbone. Although the use of viral antigens are noted above, genes encoding antigens derived from bacterial, protozoan, fungal, and/or parasitic organisms can also be incorporated into such a modified influenza virus backbone for use in vaccine preparations. It is also contemplated that other immune targets, including endogenous (i.e. human) antigens that are associated with disease states (for example, a cancer-associated antigen and/or a tau protein), can be incorporated into and expressed by this vector. As such, this platform can be employed to serve as a cancer vaccine (therapeutically and/or prophylactically) in both or either of primary prevention and preventing cancer recurrence, or, alternatively, as a treatment for Alzheimer's disease and other diseases associated with tau protein plaques.

A variety of mutations can be developed using the inventive methodologies. For example, A14U and G917A mutations, which are located within the M segment of the influenza viral genome, can support replication of DelNS1 A/WSN/33 (H1N1) and DelNS1 H7N9 virus, respectively, despite the deletion of a portion of the NS1 virulence factor gene. It should be appreciated, however, that mutations in other, non-M segment portions of the viral genome can be used. For example, in some embodiments of the inventive concept a mutation in an NP segment of an influenza virus genome can support replication of an influenza virus in which the intron encoding for the NS1 virulence factor has been excised. Such DelNS1 viruses are avirulent in mice and can render cross protection to various subtypes of influenza virus. Mutations conferring similar properties can be developed from current seasonal circulating strains of influenza virus (for example, the 2009 H1N1 viral strain that has become one of the seasonal flu viruses circulating among humans since the 2009 pandemic).

In one embodiment of the inventive concept, a DelNS1 strain was developed from such a 2009 H1N1 strain, A/California/04/09 from which an extended portion or all of the NS1 encoding intron (e.g. extending beyond the segment encompassed by nucleotides 57 to 528) has been deleted. Utilizing methods of the inventive concept a DelNS1 strain of such an influenza virus was developed with a G345A mutation within the NP region, which enable efficient replication of the DelNS1 virus in cell culture and in eggs. Surprisingly, this novel adaptive mutation was different and distinct from the M region mutations of the DelNS1 A/WSN/33 and the H7N9 viruses, and has not been previously reported as a mutation in DelNS1 influenza viruses.

Using replicative competent DelNS1 2009 H1N1 virus derived from the A/California/04/09 strain, methods of the inventive concept have successfully produced DelNS1 cold adapted H1N1 vaccine strains, for example cold adapted CA4-DelNS1. Surprisingly this double modification can provide an influenza virus that produces a high viral titer, for example a viral titer lying in a range that can be adapted for vaccine production. It should be appreciated that prior art (i.e. commercialized) live attenuated flu vaccine (ex: Flumist®) relies on the properties of cold adapted features of a "backbone" derived from a H2N2 virus strain (A/Ann Arbor/6/60). Cold adapted live attenuated vaccines derived from this backbone are only approved by the FDA for use in the 2 years to 49 years age group. In restricting use the FDA cites concerns from use in these age groups and in groups with certain underlying conditions, as the only attenuating condition is that the vaccine strain harbors mutations that restrict replication at the higher temperature of the lower respiratory tract. Unfortunately these age groups suffer relatively high lethality on influenza infection. It should be appreciated that the dual mechanism of protection is provided to subjects receiving the vaccines developed in accordance with the inventive concept, as a DelNS1 mutation in the novel vaccine strain in combination with mutations conferring cold-adaptation provides a higher level of safety without sacrificing effectiveness.

As noted above, passage of DelNS1 strains of influenza virus having a mutation that provides replication through embryonated eggs at low (i.e. less than 37° C.) temperatures permits development of mutations that confer cold adaptation. There are a variety of mutations that can be useful in this regard. For example, the novel mutations in NEP, T261G and A310G, have been associated with the cold adapted feature of a DelNS1 H1N1 vaccine strain. Notably, these mutations are distinct and different from those present in the A/Ann Arbor/6/60 strain used as the backbone for prior art commercialized live attenuated vaccine. Surprisingly, such a DelNS1 cold adapted H1N1 virus (e.g. Ca4-DelNS1 virus) is able to replicate efficiently, and a protocol can be derived that allows stable replication of vaccine strain of such a virus in embryonated eggs. Surprisingly, replication levels similar to those of a wild type virus in eggs can be achieved.

Such cold adaptation mutations were, advantageously, found to confer growth restriction to DelNS1 cold adapted influenza virus at elevated (e.g. physiological) temperatures. For example, such a virus was found to replicate at 30° C. to 33° C. but was found to be growth restricted at 37° C. to 39° C., indicating that replication of the cold adapted CA4-DelNS1 virus can be restricted at higher temperatures such as 37° to 39° C. Such growth restriction indicates that cold adapted Del1NS1 influenza viruses of the inventive concept are suitable for use a live attenuated vaccine, in particular for use as live attenuated vaccine strains that can be effectively administered by application to mucosal tissue. Vaccine formulations produced using cold adapted DelNS1 of the inventive concept have been found to produce no apparent pathogenic effects in mice.

As shown below, vaccines prepared using cold adapted DelNS1 influenza virus of the inventive concept provide cross protection in mice challenged with lethal dose of various highly pathogenic influenza virus strains. In a number of challenges the cold adapted DelNS1 vaccine strain provides significantly better protection than that provided by prior art Flumist® cold adapted H1N1 vaccine. For example, mice immunized with cold adapted CA4-DelNS1 virus exhibited less body weight loss and higher survival rate than those mice immunized with the Flumist® Cold adapted CA7 vaccine strain. The effect is even more apparent when mice are challenged with high lethal doses of H5N1 or H7N9 virus.

EXAMPLES

Figure 1:
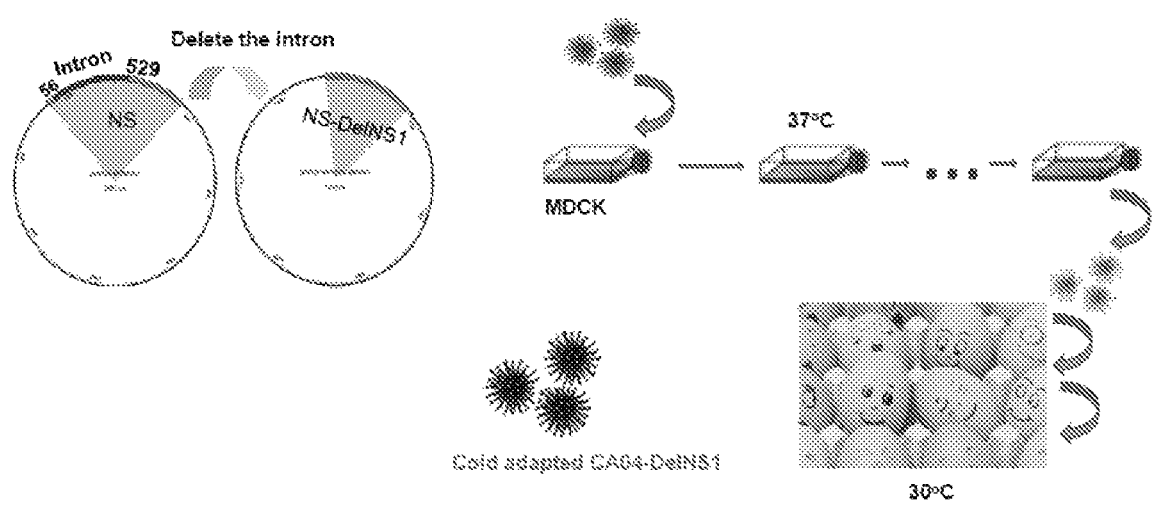

A California(CA)/04/09 strain was used for construction of CA4-DelNS1 virus through reverse genetic procedures that deleted an intron at 56-529. Rescued virus was passaged until the DelNS1 virus was stabilized by replication in MDCK cells at 37° C. After sequence confirmation of mutations, CA (cold adapted) 4-DelNS1 virus was further adapted to replicate at lower temperatures by passage at 30° C. in chicken embryonated eggs until the virus titer was stabilized. A schematic depiction of the process is shown in FIG. 1.

Sequence analysis was performed on CA4-DelNS1 following passage in MDCK cells. One adaptive substitution of G to A in the NP segment at position G346A (D101N in protein sequence) was confirmed. This substitution was found to support CA4-DelNS1 virus replication in MDCK cells and in eggs. Results of sequence analysis of non-mutated (P1) and mutated strains of the CA4-DelNS1 virus are shown in FIG. 2.

Figure 3:
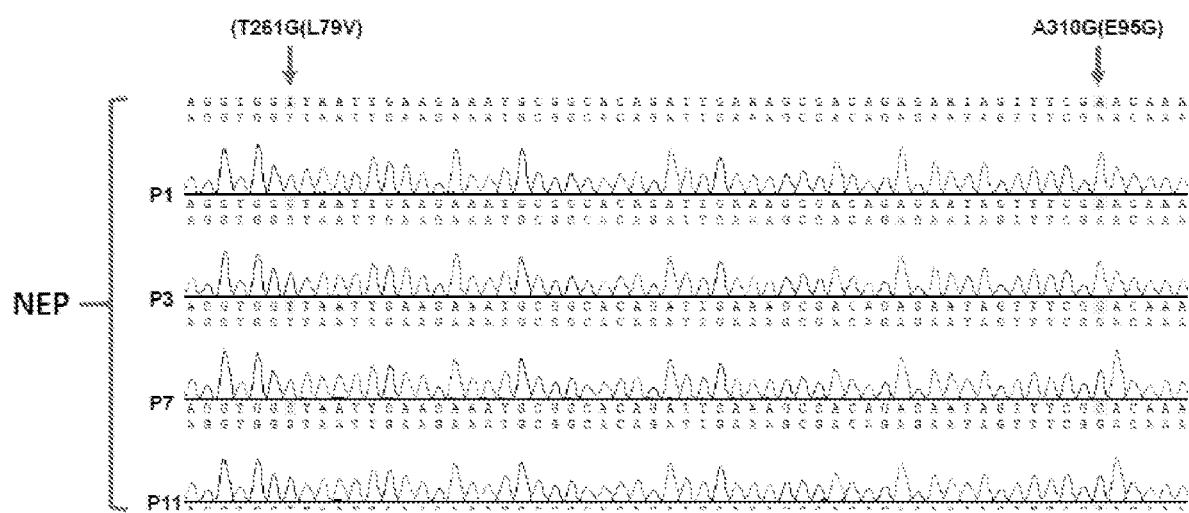
FIG. 3 depicts sequencing data showing mutations in NEP at T261G (L79V) and A310G(E95G) positions that have been found to support cold adapted DelNS1 virus replication.

Sequence analysis was performed on CA4-DelNS1 virus following cold adaptation by passage and replication stabilization in embryonated chicken eggs at 30° C. Two adaptive substitutions, T261G (L79V) and A310G (E95G), were identified and verified in the NEP coding region of NS segment. Results of sequence analysis of non-mutated (P1) and mutated strains of the CA4-DelNS1 virus are shown in FIG. 3.

Growth kinetics of the cold adapted CA4-DelNS1 virus was examined in MDCK cells after multiple cycle replication at low temperature (33° C.) and high temperature (39° C.), respectively. Results are shown in FIG. 4.

Figure 4:
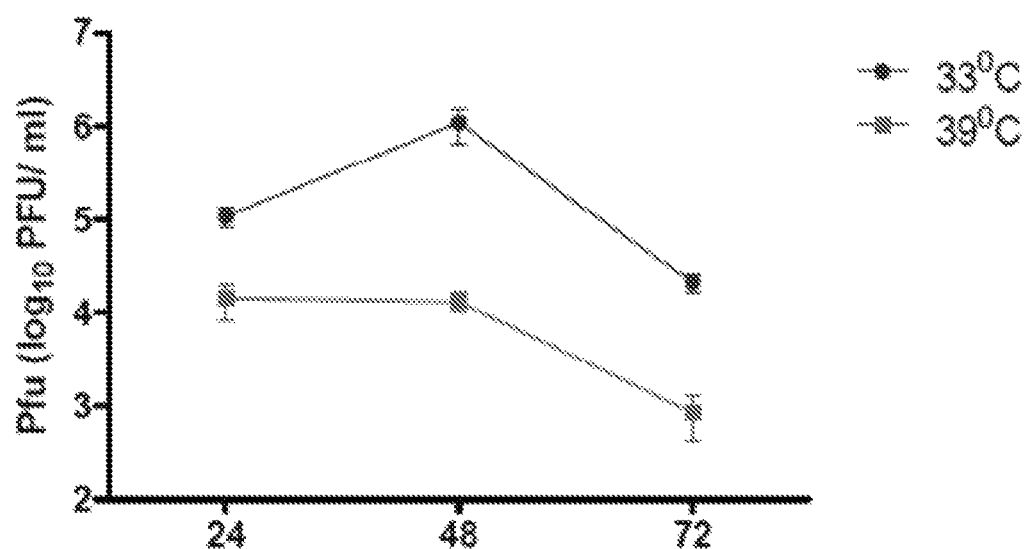
FIG. 4 graphically depicts growth properties of Cold adapted CA4-DelNS1 virus at 33° C. and 39° C.

FIG. 4. Growth properties of Cold adapted CA4-DelNS1 virus at 33° C. and 39° C.

Figure 5:
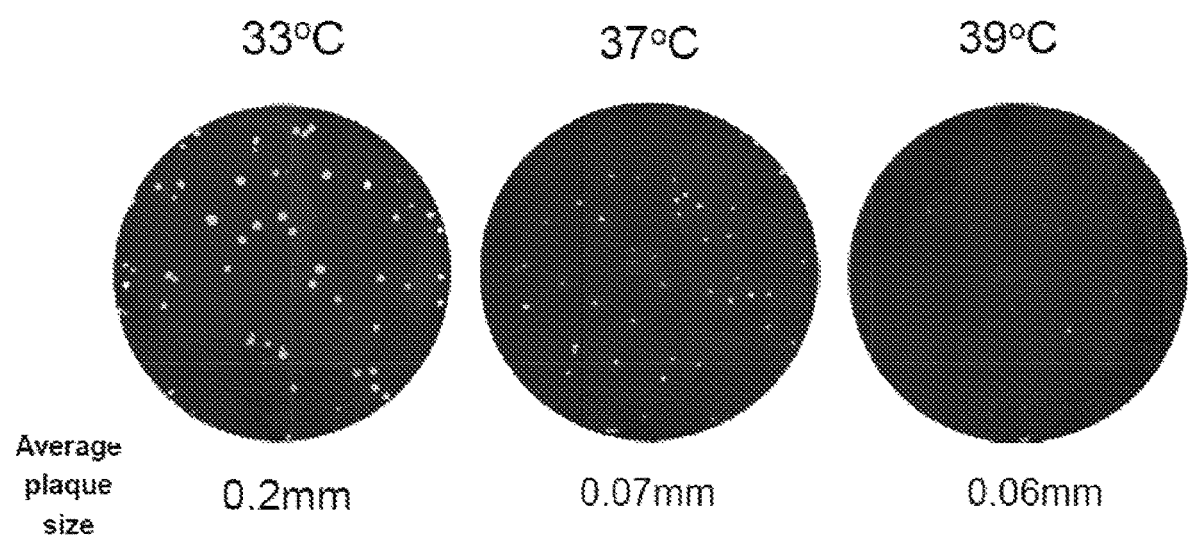
FIG. 5 shows photographs demonstrating plaque sizes of Cold adapted CA4-DelNS1 virus cultured at different temperatures.

Plaque forming properties of the cold adapted CA4-DelNS1 virus at 33° C., 37° C. and 39° C. were evaluated using MDCK cells on soft agar plates. Results are shown in FIG. 5.

Figure 6:
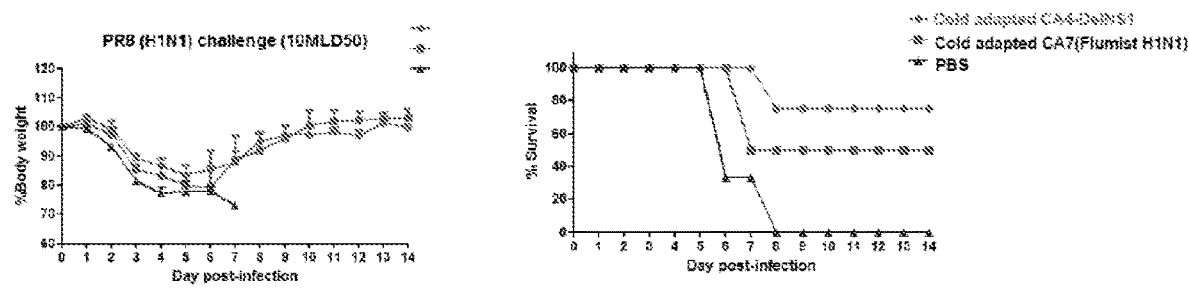
FIG. 6 shows data related to protection by a vaccine of the inventive concept to a lethal challenge of mouse adapted PR8 (H1N1) virus.

Groups of 6 mice were immunized with a single dose of cold adapted CA4-DelNS1 virus and Flumist® H1N1 vaccine using a nasal drop procedure. Two weeks after immunization the mice were challenged with a lethal inoculums (10 MLD50) of PR8 (H1N1) virus. Body weight change and survival rate were recorded for two weeks after virus challenge and shown in FIG. 6. The protective effect of nasal drop immunization with the cold adapted CA4-DelNS1 virus is evident, providing a nearly 80% survival rate.

Figure 7:
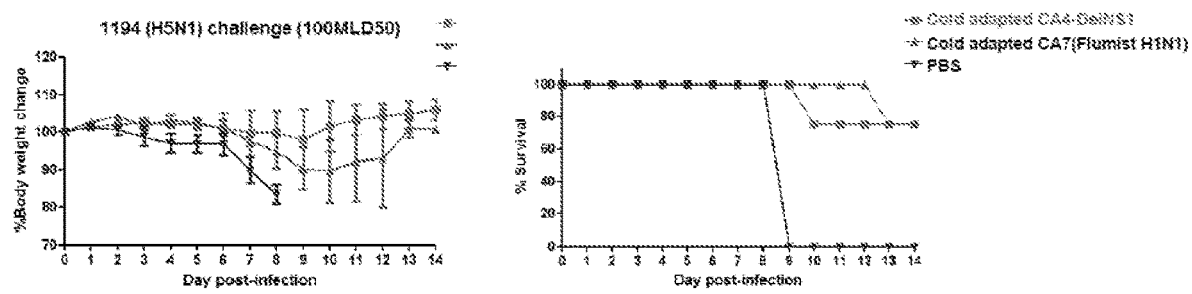
FIG. 7 shows data related to protection by a vaccine of the inventive concept to a lethal challenge of A/Vietnam/1194/04 (H5N1) virus.

Groups of 6 mice were immunized with a single dose of cold adapted CA4-DelNS1 virus and Flumist® H1N1 vaccine using a nasal drop procedure. Two weeks of immunization, mice were challenged with lethal inoculum (100 MLD50) of A/Vietnam/1194/04 (H5N1) virus. Body weight change and survival rate were recorded for two weeks after virus challenge. Results are shown in FIG. 7. The protective effect of nasal drop immunization with the cold adapted CA4-DelNS1 virus is evident, providing a nearly 80% survival rate and no significant loss of body weight.

Figure 8:
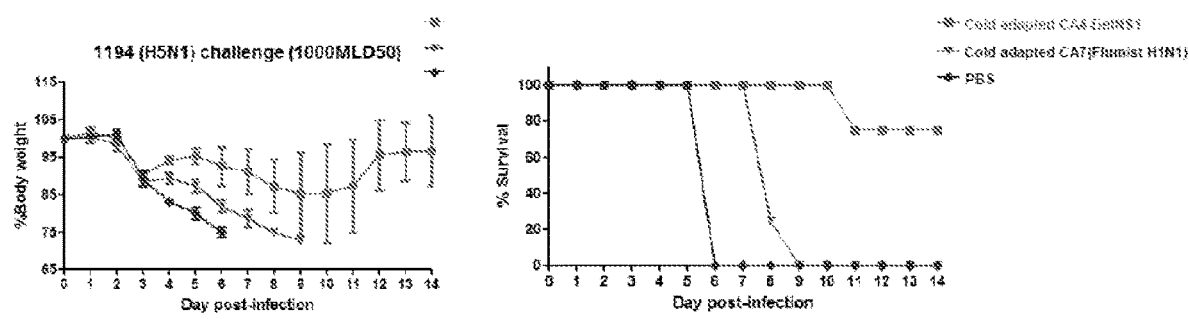
FIG. 8 shows data related to protection by a vaccine of the inventive concept to a high lethal challenge of A/Vietnam/1194/04 (H5N1) virus.

Groups of 6 mice were immunized with two doses of cold adapted CA4-DelNS1 virus and Flumist® H1N1 vaccine, two weeks apart, using a nasal drop procedure. Two weeks after the second dose, mice were challenged with high lethal inoculum (1,000 MLD50) of A/Vietnam/1194/04 (H5N1) virus. Body weight change and survival rate were recorded for two weeks after virus challenge. Results are shown in FIG. 8. The protective effect of nasal drop immunization with the cold adapted CA4-DelNS1 virus is evident, providing a nearly 80% survival rate.

Figure 9:
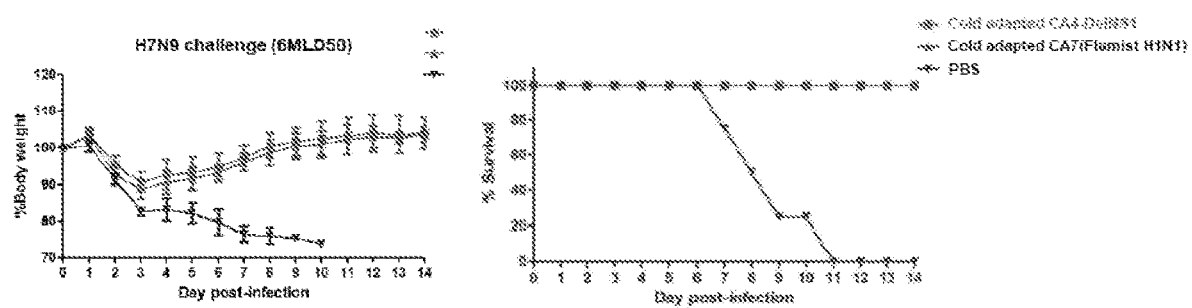
FIG. 9 shows data related to protection by a vaccine of the inventive concept to a high lethal challenge of A/Zhejiang/1/RG/2013 (H7N9) virus after a single nasal drop immunization.

Groups of 6 mice were immunized with a single dose of cold adapted CA4-DelNS1 virus and Flumist® H1N1 vaccine, using a nasal drop procedure. Two weeks after immunization, mice were challenged with high lethal inoculums (6 MLD50) of A/Zhejiang/1/RG/2013 (H7N9) virus. Body weight change and survival rate were recorded for two weeks after virus challenge. Results are shown in FIG. 9.

The protective effect of nasal drop immunization with the cold adapted CA4-DelNS1 virus is evident, with mice so immunized showing only a minor initial loss of body weight followed by rapid and complete recovery.

Figure 10:
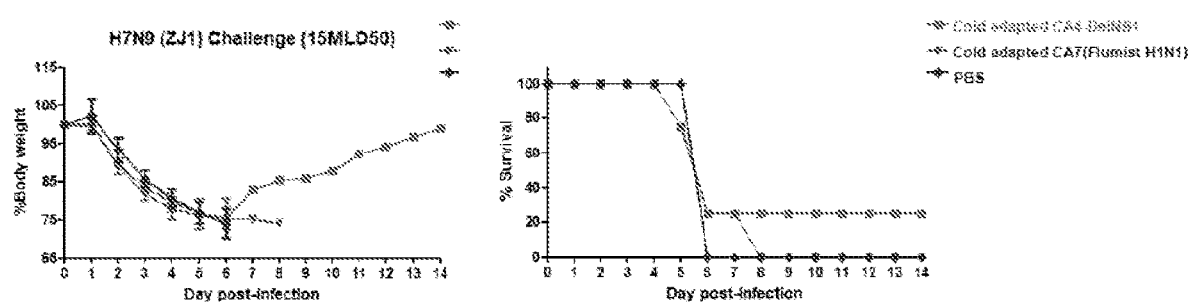
FIG. 10 shows data related to protection by a vaccine of the inventive concept to a high lethal challenge of A/Zhejiang/1/RG/2013 (H7N9) virus after two nasal drop immunizations.

Groups of 6 mice were immunized with two doses of cold adapted CA4-DelNS1 virus and Flumist® H1N1 vaccine, two weeks apart, using a nasal drop procedure. Two weeks after the second dose, mice were challenged with high lethal inoculums (15 MLD50) of A/Zhejiang/1/RG/2013 (H7N9) virus. Body weight change and survival rate were recorded for two weeks after virus challenge. The results are shown in FIG. 10. The protective effect of nasal drop immunization with the cold adapted CA4-DelNS1 virus is evident, with mice so immunized showing an almost 20% survival rate.

Figure 11:
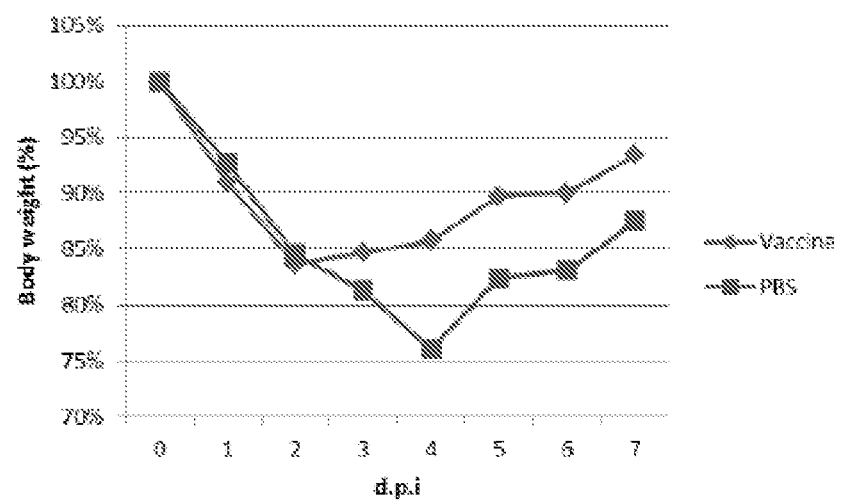
FIG. 11 shows data related to protection by immunization with cold adapted DelNS1 influenza virus carrying a gene encoding for a MERS antigen of the inventive concept to MERS.
Figure 12:
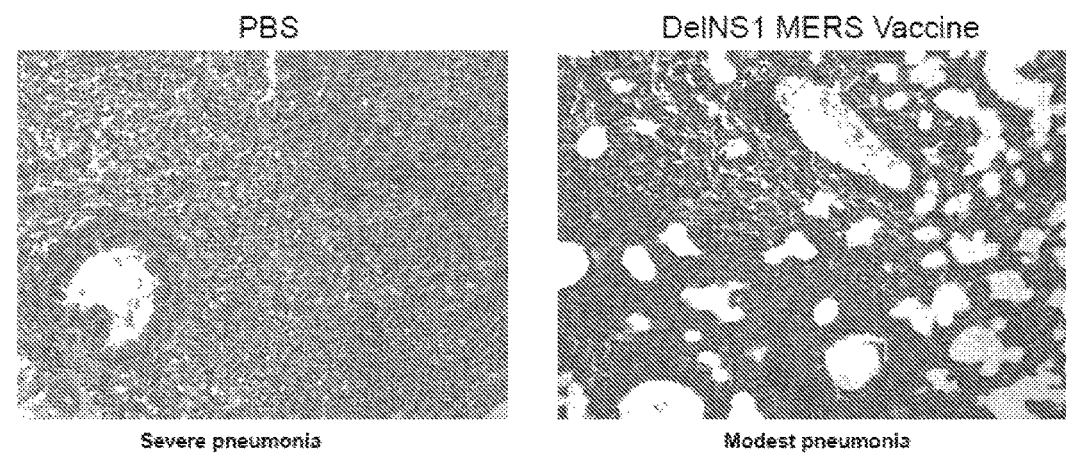

As noted above, a cold adapted, replicatively competent DelNS1 influenza virus of the inventive concept can be used as a vehicle or backbone for the development on non-influenza immunizing viral strains. For example, genes encoding for exogenous antigens associated with human pathogens (such as bacteria, fungi, and/or parasites) or endogenous (i.e. human) antigens associated with human disease (such as cancer, auto-immune disease, and neurodegenerative diseases such as Alzheimer's and Parkinson's disease) can be incorporated into the genome of a cold adapted DelNS1 influenza virus of the inventive concept. Results of studies of a vaccine prepared using a cold adapted DelNS1 influenza virus carrying an exogenous gene encoding for a MERS Coronavirus antigen are shown in FIGS. 11 and 12. As shown in FIG. 11 inoculation of mice treated with Adv-DPP4 to confer susceptibility to the MERS CoV provided protection against subsequent infection with the MERS-CoV, as evidenced by reduced weight loss and more rapid recovery relative to similarly treated, unvaccinated mice. Further evidence of protection is shown by histology studies of lung tissue, as shown in FIG. 12. As shown mice receiving a sham vaccination with PBS show evidence of severe pneumonia following infection with MERS, whereas mice receiving a vaccine including a cold adapted DelNS1 influenza virus carrying a gene encoding for a MERS antigen developed only moderate pneumonia.

Protocols

DelNS1 Virus Adaptation

1. Construction of NS1 Deletion Plasmid:

2009 H1N1 A/California/04/09 (CA4) was used as backbone to construct the DelNS1 vaccines strain. Plasmid without NS1 expression was constructed by inverse PCR with primers as follows:

```
CA04-DelNS1-529F:
GACATACTTATGAGGATGTC

CA04-DelNS1-56R:
CTGAAAGCTTGACATGGTGTTG
```

2. Rescue of CA04-DelNS1 Virus:

Nine plasmids: pHW2000-CA04-PB2, pHW2000-CA04-PB1, pHW2000-CA04-PA, pHW2000-CA04-NP, pHW2000-CA04-HA, pHW2000-CA04-NA, pHW2000-CA04-M, pHW2000-CA04-DelNS1 and pCX-CA04-NS1 were mixed together in one tube. Each one is present at 1 µg. Transfection with the mixed plasmids was conducted in 80% confluent 293T cells plated in a 6-well plate. During transfection the old medium was replaced with 1 ml Opti-MEM without penicillin and streptomycin. Sixteen hours later the supernatant was discarded and 2 ml of MEM containing 1 µg/ml trypsin was added. Seventy hours after transfection, the supernatant was collected after the cell debris was removed.

3. Passage of DelNS1 Virus:

Two hundred microliter rescued DelNS1 virus was injected into a 9 to 10-day-old fertilized egg and incubated in the 37° C. incubator for 48 hours. Egg allantoic fluid was collected and HA titer was measured. Blood cells and other debris were removed by centrifugation at 1,500 g for 10 minutes. Supernatant was transferred into a Millipore 100K ultra filter and centrifuged at the speed of 3,000 g for 10 minutes. PBS was added to the filter to give a volume of 10 ml to wash the concentrated virus, and the suspension was again centrifuged at 3,000 g for 10 minutes. Two hundred microliter of the resulting virus preparation is used to inoculate 9 to 10-day-old fertilized eggs and the procedure was repeated until the virus HA titer increased dramatically.

4. Sequence Analysis of DelNS1 Virus:

After the virus HA titer becomes stable, the viral RNA was extracted and the full genome was sequenced in order to check the mutation site.

5. Introduction of the Mutation(s) Discovered in the Adapted Virus to the Backbone Plasmids:

The adaptive mutation identified was introduced into wild type CA4 virus to confirm the role of the substitution in supporting virus replication using standard site-mutagenesis protocol.

6. The DelNS1 Virus was Re-Rescued with the Mutated Plasmids.

Growth Kinetics in Cells and Eggs

For MDCK Cells:

The 100% confluent MDCK cells plated in the 24 well plate were infected with DelNS1 viruses at an MOI of 0.05 at 37° C. One hour after absorption, the supernatant was removed and then the cells were washed once with 500 µl PBS per well. The cells were overlaid with MEM supplemented with 1 µg/ml trypsin; then the cells were incubated at 37° C. or 33° C. The supernatant were collected at the corresponding time points and then was centrifuged to remove the cells and stored at −80° C. for plaque assay.

For Eggs:

The 9 to 10-day-old eggs were inoculated with 1,000 PFU of DelNS1 viruses. The eggs were incubated at 37° C. or 33° C. The allantoic fluid was collected at the corresponding time points.

Plaque Assay

Ten fold diluted DelNS1 virus were used to infect 100% confluent MDCK cells plated in six-well plates and were incubated the cells at 37° C. One hour after adsorption, the supernatant was discarded and the cells were washed once with 1 ml of PBS. The cells were overlaid with 1% MEM agarose supplemented with 1 µg/ml trypsin, and then the plate were placed upside down inside a at 33° C. incubator. Forty eight hours later, the cells were fixed with 10% formalin for at least 1 hour and then the formalin and the agarose gel were discarded. The cells were stained with 1% crystal violet to visualize the plaques.

Mouse Studies

Six to eight-week old female BALB/C mice were anesthetized and then inoculated intranasally with 25 µl of PBS containing $1.35 \times 10^5$ PFU of DelNS1 virus. Mouse body weight and other parameters are recorded daily for two weeks following inoculation. For determination of lung titer after infection, mice were euthanized 3 days post-infection. Two weeks after immunization, mice were challenged with the corresponding lethal dose viruses. Mouse body weight was recorded every day for two weeks. After virus challenge, mice were euthanized when the body weight loss is greater than 25%.

MERS Vaccine Protocols

Construction of the pHW2000-MERS-RBD-NEP Plasmid

To generate recombinant NS1-deleted influenza virus expressing MERS receptor binding domain (RBD), the plasmid pHW2000-MERS-RBD-NEP plasmid was constructed. It has an open reading frame which is composed of CA04 N terminal of NS1, MERS RBD domain, PTV1-2A cleavage site, CA04 NEP with the mutated N terminal NS1 sequence. The sequence of MERS-RBD-PTV1-2A was amplified by PCR from the plasmid pcDNA-MERS-SPIKE. The PCR product was then inserted into the pHW2000-CA04-DelNS1, which contains only CA04 NEP open reading frame, by ligation independent cloning using exonuclease III. After transformation, plasmids were extracted from right clones and subsequently sequenced to confirm the sequence.

Rescue of the CA04-delNS1-RBD Virus

Nine plasmids: pHW2000-CA04-PB2, pHW2000-CA04-PB1, pHW2000-CA04-PA, pHW2000-CA04-NP, pHW2000-CA04-HA, pHW2000-CA04-NA, pHW2000-CA04-M, pHW2000-MERS-RBD-NEP and pCX-CA04-NS1, each with 1 μg, were mixed and used to transfect 80% confluent 293T cells in a 6-well plate. During transfection the old medium was replaced with 1 ml of Opti-MEM without antibiotics. Sixteen hours later the supernatant was discarded and 2 ml of MEM containing 1 μg/ml trypsin was added. Seventy hours after transfection, the supernatant was collected after the cell debris is removed. The supernatant was injected into 9 to 10-day-old fertilized eggs and incubated at 37° C. for 48 hours. Egg allantoic fluid was collected, and cleared by centrifugation. The virus was then sequenced and titered by plaque assay in MDCK cells. The highest titer of the CA04-delNS1-RBD virus is $2 \times 10^7$ pfu/ml.

Animal Studies

Two groups (six each) of six to eight-week old female BALB/C mice are anesthetized and then inoculated intranasally with 25 μl PBS containing $5 \times 10^5$ $TCID_{50}$ of MERS-RBD-DelNS1 virus, twice in two weeks apart. Five days before MERS coronavirus challenge, mice were inoculated with $2.5 \times 10^8$ PFU of Adv-DPP4 in 50 μl PBS. On day 5 post infection of Adv-DPP4, mice were challenge with $5 \times 10^5$ $TCID_{50}$ MERS coronavirus. One group of mouse are recorded daily for body weight change for two weeks. Another group of mouse were sacrificed on day 3 post challenge of MERS coronavirus and lung tissues were obtained for histopathological examination and virus titer analysis It should be apparent to those skilled in the art that many more modifications besides those already described are possible without departing from the inventive concepts herein. The inventive subject matter, therefore, is not to be restricted except in the spirit of the appended claims. Moreover, in interpreting both the specification and the claims, all terms should be interpreted in the broadest possible manner consistent with the context. In particular, the terms "comprises" and "comprising" should be interpreted as referring to elements, components, or steps in a non-exclusive manner, indicating that the referenced elements, components, or steps may be present, or utilized, or combined with other elements, components, or steps that are not expressly referenced. Where the specification claims refers to at least one of something selected from the group consisting of A, B, C . . . and N, the text should be interpreted as requiring only one element from the group, not A plus N, or B plus N, etc.

What is claimed is:

1. A mutated influenza A H1N1 virus for vaccine production, comprising:
- a modified H1N1 influenza virus genomic segment comprising a deletion of NS1 virulence factor activity, wherein the deletion of NS1 virulence factor activity comprises a deletion of at least part of an NS1 virulence factor gene;
- a first set of one or more mutation(s) within the modified H1N1 influenza virus' nucleoprotein (NP) genomic segment, wherein the first set of one or more mutation(s) comprises a first set of one or more point mutation(s) that confer replicative competence, wherein the first set of one or more point mutations comprises a G346A mutation in the H1N1 influenza virus NP genomic segment; and
- a second set of one or more mutation(s) within the modified H1N1 influenza virus' nuclear export protein (NEP) genomic segment, wherein the second set of one or more mutation(s) comprises a second set of one or more point mutation(s) selected from the group consisting of a T261G and an A310G mutation in the H1N1 influenza virus genomic segment encoding NEP:
wherein the genomic segments are full-length.

2. The mutated influenza virus of claim 1, wherein the deletion of NS1 virulence factor activity comprises a deletion of at least part of the NS1 virulence factor gene extending beyond nucleotides 57 to 528 of an NS1 segment of the mutated virus.

3. The mutated influenza virus of claim 1, further comprising an insertion of a gene encoding for an exogenous antigen.

4. The mutated influenza virus of claim 3, wherein the exogenous antigen is derived from a human pathogen.

5. The mutated influenza virus of claim 4, wherein the human pathogen is a virus.

6. The mutated influenza virus of claim 5, wherein the virus is a SARS coronavirus or MERS coronavirus.

7. A live, attenuated vaccine comprising:
- a therapeutically effective amount of the modified H1N1 influenza virus of claim 1,
- and a vehicle.

8. The live, attenuated vaccine of claim 7, wherein the vehicle comprises a TLR-7 agonist.

9. The live, attenuated vaccine of claim 7, wherein the live, attenuated vaccine is safe for use in a human under two years of age.

* * * * *